United States Patent [19]
McMichael

[11] Patent Number: 6,096,721
[45] Date of Patent: *Aug. 1, 2000

[54] METHOD FOR TREATING MUCOSITIS BY SUBLINGUAL ADMINISTRATION OF DNA

[75] Inventor: John McMichael, Delanson, N.Y.

[73] Assignee: Milkhaus Laboratory, Inc., Delanson, N.Y.

[ * ] Notice: This patent is subject to a terminal disclaimer.

[21] Appl. No.: 09/037,895

[22] Filed: Mar. 10, 1998

Related U.S. Application Data

[63] Continuation-in-part of application No. 08/755,092, Nov. 22, 1996, Pat. No. 5,726,160, which is a continuation of application No. 08/421,232, Apr. 13, 1995, abandoned.

[51] Int. Cl.⁷ .................................................... A61K 48/00
[52] U.S. Cl. ................................................................. 514/44
[58] Field of Search ................................................. 514/44

[56] References Cited

U.S. PATENT DOCUMENTS

| | | | |
|---|---|---|---|
| 5,240,846 | 8/1993 | Collins et al. | 435/240.1 |
| 5,292,498 | 3/1994 | Boucher, Jr. | 424/45 |
| 5,420,116 | 5/1995 | Puchelle et al. | 514/47 |
| 5,470,838 | 11/1995 | von Borstel et al. | 514/50 |
| 5,726,160 | 3/1998 | McMichael | 514/44 |

FOREIGN PATENT DOCUMENTS

| | | |
|---|---|---|
| WO 92/11016 | 7/1992 | WIPO . |
| WO 93/12240 | 6/1993 | WIPO . |
| WO 94/23048 | 10/1994 | WIPO . |
| WO 95125800 | 9/1995 | WIPO . |
| WO 96/32138 | 10/1996 | WIPO . |
| WO 96/40059 | 12/1996 | WIPO . |
| WO 97/05195 | 2/1997 | WIPO . |

OTHER PUBLICATIONS

Canonico, A.E. et al., "Expression of a CMV Promoter Driven Human α-1 Antitrypsin Gene in Cultured Lung Endothelial Cells and in the Lungs of Rabbits," *Clin Res.*, 39(2): 219A (1991).

Ledley, F.D., "Non-viral gene therapy," *Current Opinion in Biotechnology*, 5:626–636 (1994).

Ledley, F.D., "Nonviral Gene Therapy: The Promise of Genes as Pharmaceutical Products," *Human Gene Therapy*, 6: 1129–1144 (Sep., 1995).

Marshall, E., "Gene Therapy's Growing Pains," *Science*, 269: 1050–1055 (Aug. 25, 1995).

Rosenfeld, M.A. et al., "Adenovirus–Mediated Transfer of a Recombinant α1–Antitrypsin Gene to the Lung Epithelium in Vivo," *Science*, 252: 431–434 (Apr. 19, 1991).

Aalton, E.W.F.W. et al., "Noninvasive liposome–mediated gene delivery can correct the ion transport defect in cystic fibrosis mutant mice," *Chemical Abstracts*, 119(21):62 (Nov. 22, 1993) (Abstract 217089w).

Flotte, T.R., et al., "Stable in vivo expression of the cystic fibrosis transmembrane conductance regulator with an adeno–associated virus vector," *Chemical Abstracts*, 120(5):229 (Jan. 31, 1994) (Abstract 46918e).

Baker, R.C., "Pitfalls in Diagnosing Acute Otitis Media," *Pediatric Annals*,20:591–593, 596–598 (Nov., 1991).

Berman, S., "Otitis Media in Developing Countries," *Pediatrics*, 96(1):126–131 (Jul., 1995).

Dagan, R. et al., "Treatment Failures in Otitis Media—What Can We Learn," *Ear, Nose and Throat J.*, 77(6 Suppl):16–21 (Jun. 1998).

Karver, S.B., "Otitis Media," *Ear, Nose and Throat Disorders*, 25(3):619–632 (Sep., 1998).

Klein, J.O., "Otitis Media," *Clinical Infectious Disease*, 19:823–833 (1994).

Rosenfeld, J. et al., "Acute Otitis Media in Children," *Primary Care; Clinics in Office Practice*, 23(4):677–686 (Dec. 1996).

Textbook or Respiratory Medicine, John F. Murray, ed., W.B. Saunders Company, Philadelphia, Pa., p. 1038. 1988.

*Primary Examiner*—Deborah Crouch
*Assistant Examiner*—Michael C. Wilson
*Attorney, Agent, or Firm*—Marshall, O'Toole, Gerstein, Murray & Borun

[57] ABSTRACT

Methods for treating mucositis are presented. An effective amount of DNA is administered to a patient with mucositis sublingually in a manner that does not cause gene transfer but does cause a reduction in viscosity of mucous or sputum.

5 Claims, No Drawings

METHOD FOR TREATING MUCOSITIS BY SUBLINGUAL ADMINISTRATION OF DNA

This application is a continuation-in-part of U.S. patent application Ser. No. 08/755,092 filed Nov. 22, 1996, issued Mar. 10, 1998 as U.S. Pat. No. 5,726,160 which is a continuation of U.S. patent application Ser. No. 08/421,232 filed Apr. 13, 1995, now abandoned.

FIELD OF THE INVENTION

The present invention relates to methods for treatment of pulmonary disorders.

BACKGROUND OF THE INVENTION

The present invention provides methods for treatment of pulmonary diseases. Such diseases, including cystic fibrosis, emphysema, chronic bronchitis, sinusitis, and the common cold, have in common bronchial or sinus congestion, production of large amounts of sputum, and the possibility of secondary bacterial infection requiring antibiotic therapy. The most serious of those diseases is cystic fibrosis, a genetic disorder of exocrine function characterized by abnormally viscous mucus secretions leading to chronic pulmonary obstruction, pancreatic insufficiency and elevated sweat sodium and chloride levels. Cystic fibrosis is often fatal. The viscosity of sputum produced by cystic fibrosis patients is thought to be due to its high content of DNA. Diseases such as bronchitis, emphysema, sinusitis, and the common cold are generally less severe than cystic fibrosis, but those diseases also may result in production of large amounts of sputum. Still other pulmonary diseases include mucositis (inflammation of the mucosal membranes) which is frequently associated with radiation therapy and which is characterized by production of a thick water deficient mucous which is difficult for the subject to eliminate.

Other pulmonary diseases include chronic obstructive pulmonary diseases (COPDs) which share the common feature of chronic expiratory airflow limitation i.e., persistent slowing of the rate at which exhalation can be achieved. Common COPDs include chronic bronchitis, emphysema and asbestosis and are characterized by respiratory distress but not associated with aberrant mucous accumulation. Cigarette smoke is the most common cause of COPDs which are also associated with exposure to respirable dusts particularly in workplace environments of those engaged in occupations such as gold and coal mining, textile manufacturing and cement and steel making.

As with cystic fibrosis, other pulmonary diseases frequently lead to secondary bacterial infections. Treatment of pulmonary diseases generally requires antibiotic therapy which is frequently ineffective. Recently, however, cystic fibrosis has been treated using DNase. The rationale for such therapy is that degrading DNA in sputum reduces the viscosity of the sputum and results in an increased ability of the patient to evacuate sputum from the lungs and nasal passages. However, no known report advocates using DNA itself as a treatment for any pulmonary infection or condition.

SUMMARY OF THE INVENTION

The present invention provides methods for treating respiratory illness. Specifically, the invention provides methods for treating symptoms of respiratory distress not associated with aberrant mucous accumulation in a patient, comprising the step of administering in a manner so as not to effect gene transfer an effective amount of DNA in a pharmaceutically-acceptable vehicle to a patient having a disease characterized by respiratory distress not associated with aberrant mucous accumulation including but not limited to diseases such as chronic obstructive pulmonary disease including bronchitis, emphysema and asbestosis as well as asthma.

The invention further provides methods for relieving respiratory congestion in a patient as a result of overproduction of viscous mucus or sputum lodged in the patients's respiratory tract due to conditions including mucositis such as caused by radiation comprising the steps of administering in a manner so as not to effect gene transfer a therapeutically effective amount of DNA in a pharmaceutically-acceptable vehicle to a patient having a disease characterized by respiratory congestion, wherein said respiratory congestion is a result of an overproduction of viscous mucus or sputum lodged in said patients's respiratory tract, and wherein said method results in the reduced viscosity of said mucus or said sputum such that there is an increase of production and a reduced accumulation of mucus in said patient's respiratory tract.

Methods of the invention comprise administration to a patient suffering from respiratory distress an effective amount of DNA. The DNA is preferably provided in an amount ranging from about 0.00012 mg to about 0.003 mg and is preferably formulated in a liquid vehicle and provided at a concentration of approximately 0.0006 mg as single drops. A preferred route of administration is sublingual, but other routes, such as subcutaneous, intravenous, intramuscular, and intrathecal are expected to work. DNA for use in the present invention may be prokaryotic DNA or eukaryotic DNA and may be formulated in a number of pharmaceutically-acceptable vehicles, including water, saline, albumin, and dextrose.

Additional aspects and advantages of the invention will become apparent upon consideration of the following detailed description thereof.

DETAILED DESCRIPTION OF THE INVENTION

The present invention provides methods for treating patients with symptoms of respiratory distress not associated with aberrant mucous accumulation in a patient including symptoms resulting from chronic obstructive pulmonary diseases such as chronic bronchitis, emphysema, by administering to such patients a small amount of DNA in a manner so as not to effect gene transfer. Methods of the invention are also useful for treating pulmonary congestion in patients having any disease in which mucus production is a symptom and are especially effective in treating diseases wherein viscous mucus or sputum is produced and becomes lodged in a patient's respiratory tract. In those cases, methods of the invention reduce production of DNA in a patient's mucus secretions and thereby render mucus less viscous, allowing for increased production away from the respiratory tract.

Methods according to the invention for treating pulmonary congestion have been tested in clinical trials with human patients having various respiratory disorders, including cystic fibrosis, bronchitis, and emphysema using calf thymus DNA (Sigma, St. Louis). In each case, patients are administered sublingual drops of DNA at a concentration of about 0.0006 mg DNA per drop. No other therapy was conducted in any patient during the course of DNA therapy. As noted below, all patients tested showed improvement in mucus production (i.e. sputum was easier to dislodge) from the respiratory tract. In addition, sputum was less viscous as compared to pretreatment levels. Reduced sputum viscosity leads to increased patient comfort, increased ability of the patient to breathe, and reduced risk of secondary bacterial infection. No adverse side effects were observed in any patients. Drops of DNA may be administered at the appropriate concentration in doses of 1 to 10 drops per day as required by the patient. For each Example below, calf thymus DNA (Sigma) was used.

The following Examples illustrate the preferred embodiments of the invention and provide evidence of the effectiveness of claimed treatment methods. Numerous improvements and further aspects of the invention are apparent to the skilled artisan upon consideration of the Examples which follow.

EXAMPLE I

Twenty-three year-old twin brothers presented with cystic fibrosis. Each had a history of hospitalizations for lung clearance and secondary infections diagnosed as being associated with their cystic fibrosis. Each patient began therapy with 1–2 drops (0.0006 mg/drop) of DNA sublingually per day. For almost two years since beginning DNA therapy, neither patient has been hospitalized. In addition, follow-up evaluations by physicians revealed a 30–45% increase in airflow in each patient. Moreover, forced vital capacity, a common measure of lung capacity and the extent of mucus clearance in the lungs, increased from 60–90%. Finally, each of the brothers has gained weight and has shown increased expectoration.

After approximately one year of therapy, one of the brothers stopped taking the DNA drops. His condition steadily worsened as a result, with increased mucus viscosity, decreased forced vital capacity and reduced expectoration. That patient then began taking drops of DNA at the prescribed dose and immediately improved to the condition he was in prior to the time at which he stopped taking the drops.

EXAMPLE II

A 64-year-old female patient who suffered from emphysema and bronchitis, as diagnosed by her physician, was placed on a dose of 1 drop per day (0.0006 mg/drop) of DNA sublingually. Within one week, a follow-up evaluation revealed that her mucus production was less viscous and expectoration was increased.

EXAMPLE III

A 25-year-old female diagnosed with chronic upper respiratory illness was treated with methods according to the invention. Previous antibiotic therapy was unsuccessful in treating her condition. She began with 1 drop of DNA (0.0006 mg/drop) sublingually four times per day. Within one day, she experienced an increase in expectoration and, after three days she was able to discontinue treatment, having been completely relieved of congestion. She has remained symptom free.

EXAMPLE IV

A 32-year-old female nurse presented with a severe upper respiratory infection and unproductive respiratory congestion. She was placed on 1 drop of DNA (0.0006 mg/drop) four times per day. Her congestion began to break up almost immediately. Expectoration was improved and the patient's illness resolved after 4.5 days and no congestion recurred.

EXAMPLE V

A 63-year-old woman presented with chronic sinusitis. Four drops of DNA per day were administered. After 3 months, the patient's mucus had thinned and her cough was more productive.

EXAMPLE VI

A 37-year-old female presented with unresolved respiratory congestion. Traditional therapy, including expectorants, failed to improve her condition. The patient was then prescribed four drops of DNA (0.0006 mg/drop) per day. After one day of treatment, her congestion was more productive and sinus drainage had begun where none was present prior to treatment according to the invention.

EXAMPLE VII

A 40-year-old woman with unproductive upper respiratory congestion was placed on 4 drops of DNA (0.0006 mg/drop) per day. Her congestion was more productive after one day and she continued to expectorate freely. In this case, therapy was supplemented with an over-the-counter expectorant.

EXAMPLE VIII

A 38-year-old woman with acute and chronic respiratory disease due to exposure to toxic corrosive materials was treated with methods according to the invention. Prior to such treatment, symptoms, including chronic rhinorrhea, chest congestion and chronic respiratory infections were treated with numerous courses of antibiotics without success. The patient began treatment with 0.5 cc Q.I.D. daily and was instructed to administer treatment up to 5–6 times daily if necessary.

Upon commencing treatment according to the invention, the patient was able to produce sputum almost immediately. Continued treatment has alleviated symptoms of chronic respiratory illness.

EXAMPLE IX

A 58-year-old woman diagnosed with a childhood history of asthma and persistent adult rhinitis and sinusitis presented for treatment. Physical examination indicated clear rhinorrhea, and 3+ red throat. Nasal spray and prednisone were prescribed for 7 days. That course of treatment resulted in mild improvement. However, the patient's cough was still unproductive. Therapy according to the invention was begun at 0.5 cc Q.I.D. Within 48 hours, the patient showed improvement in the form of a productive cough and sinus drainage.

EXAMPLE X

A 48-year-old woman with chronic sinusitis and bronchitis characterized by chronic head congestion, nasal obstruction, and coughing presented for treatment according to the invention. The patient was treated according to the invention with one drop per day of DNA (0.0006 mg/drop). Treatment resulted in an overt increase in sinus and chest drainage. Upon cessation of treatment according to the invention, the patient's condition regressed. Beginning therapy again caused a similar increase in drainage and relief of congestion as seen previously with treatment according to the invention.

The following examples report the results of treatment of subjects suffering from radiation induced mucositis with the DNA containing compositions of the invention.

EXAMPLE XI

According to this example, a subject suffering from radiation induced mucositis was treated with one drop of DNA (0.0006 mg/drop) sublingually four times per day. The subject experienced a 50% improvement with phlegm thickness and had less cough. Experimentation by the subject with dosage frequency revealed that administration of one drop alone was insufficient but that administration of three to four drops per day appeared to be optimal.

EXAMPLE XII

According to this example, a subject suffering from radiation induced mucositis was treated with one drop of DNA (0.0006 mg/drop) sublingually four times per day. While treatment with four drops per day did not provide subjective improvement an increase in dosage to ten drops per day may have resulted in less phlegm. The subject discontinued administration of DNA but restarted use later and reported thinning of phlegm. The formulation was later modified to include 2 units of streptolysin O per drop although it could not be determined if incorporation of streptolysin 0 improved the therapeutic results.

EXAMPLE XIII

According to this example, a subject suffering from radiation induced mucositis was treated with one drop of DNA (0.0006 mg/drop) sublingually four times per day with the result of a 50% improvement in phlegm thickness. In addition the subject noted that her sense of taste improved from nonexistent to normal.

The following examples report the results of treatment of three patients suffering with mild to moderate chronic obstructive pulmonary disease not characterized by aberrant mucous accumulation who were successfully treated with DNA containing compositions according to the methods of the invention.

EXAMPLE XIV

A 67 year-old male former smoker with a medical history of gout, hypertension, peptic ulcer and chronic obstructive pulmonary disease presented with shortness of breath during high humidity, walking up a half flight of stairs, walking in the yard and at night laying flat in bed. The subject suffered from minimal phlegm production which was white in color. The subject was being treated with allopurinol, Pepcid (famotidine), Slobid (theophylline), Calan (verapamil HCI), Accupril (quanapril HCI) and Albuterol Inhaler. A pre-study office spirometry showed moderate COPD with an Fev1 % of 51.

The subject was treated with 1 drop of DNA (0.0006 mg/drop) sublingually four times per day. After fourteen days of treatment the subject reported that his overall dyspnea had improved from a subjective rating of a 10 to a 4. He was able to walk at the mall without shortness of breath where previously, he had to stop. A spirometry on day 16 showed no change but three months later with continued treatment according to the invention could ascend 13 steps where prior to treatment he had been unable to ascend only half as many steps without dyspnea. The subject was also able to decrease Albuterol administration from daily to 2–3 times weekly and eventually to once in four weeks and discontinue use of Slobid. The subjects wife reported that the subject's sleep is more restful and that she no longer hears wheezing at night.

EXAMPLE XV

A 71 year-old female with a medical history of hypertension, myocardial infarction, renal insufficiency, hiatal hernia, spinal stenosis, hyperlipidemia and chronic obstructive pulmonary disease presented with shortness of breath while cooking meals, walking 17 steps, carrying laundry, vacuuming, making her bed, walking to the car, and in the mall. She also complained of minimal phlegm. She was undergoing treatment with medications including Cardizem CD (ditiazem HC1), Vasotec (enalaprilat), Zocor (simvastatin), Ogen (estropripate), Zantac (ranitidine HC1), Toprol (metoprolol succinate), Nitroglycerine patch, LorTab (hydrocodone bitartrate and aspirin), and a sleep agent as required. Upon examination, she had mild anterior wheezing and a pre-study office spirometry showed an Fev1 of 70.

The subject was treated with 1 drop of DNA (0.0006 mg/drop) sublingually four times per day. After seven days of treatment the subject reported no improvement but fourteen days of treatment reported that she could walk in the mall without shortness of breath and was vacuuming and making her bed without needing to stop and rest. A repeat spirometry after fourteen days showed an Fev1 % of 78, an 11% improvement from the pre-study result. The subject's condition continued to improve except when she decreased the treatment schedule to once per day and her shortness of breath returned. After increasing back to treatment four times daily her dyspnea resolved to the extent that she was able to discontinue her use of a Serevent (Glaxo) aerosol inhaler after four months.

EXAMPLE XVI

A 76 year-old female with a medical history of hypertension, arrhythmia, hypercholesterolemia, chronic obstructive pulmonary disease (for at least ten years) and anxiety presented with dyspnea after climbing one flight of stairs, exertional dyspnea and cough and with minimal phlegm. The subject was being treated with Normodyne (labetalol HCI), Procardia (nifedipine), Persantine (dipyridamole), Zocor (simvastatin), Atrovent Inhaler (ipratropium bromide) and Xanax (aprazolam). Upon examination, she had moderately decreased lung sounds with normal blood pressure. A spirometry conducted ten years previously showed an Fev1 % of 73 (normal) with diminished mid flow rates suggesting early COPD.

The subject was treated with 1 drop of DNA (0.0006 mg/drop) sublingually twice daily and after one month of treatment had less coughing and diminished wheezing at home when in bed. A spirometry after almost two months of treatment showed an Fev1 % of 65. The subject continued to report subjective improvement and stopped administration of Atrovent. After four months wheezing was nearly gone and her cough was less than prior to treatment according to the invention.

EXAMPLE XVII

According to this example, several asthma patients were treated by daily administration of at least one drop of DNA (0.0006 mg/drop) derived from either salmon sperm or bovine sources. Follow-up evaluation of those subjects showed decreased viscosity and volume of sputum. In addition, the salmon sperm DNA was found to have therapeutic activity equivalent to that of the bovine derived DNA.

EXAMPLE XVIII

According to this example, a 56 year old non-smoker with chronic obstructive pulmonary disease/emphysema secondary to asbestosis and total disability due to pulmonary insufficiency was treated by sublingual administration of at least one drop of DNA (0.0006 mg/drop) four times daily.

After a few weeks of treatment the subject reported feeling "dramatically better" and "not out of breath." The subject has since reduced the frequency of treatment to one drop daily.

The invention has been described in terms of its preferred embodiments and is only intended to be limited by the scope of the following claims.

What is claimed is:

1. A method for treating mucositis of the respiratory tract in a patient comprising the step of administering sublingually and in a manner so as not to effect gene transfer and expression, a therapeutically effective amount of DNA in a pharmaceutically acceptable vehicle to a patient having mucositis of the respiratory tract characterized by overproduction of viscous mucous or sputum lodged in said patient's respiratory tract, and wherein said method results in the reduced viscosity, increased elimination and/or decreased accumulation of said mucus or said sputum.

2. The method according to claim 1, wherein said vehicle is selected from the group consisting of water, saline, albumin, or dextrose.

3. The method according to claim 1, wherein said effective amount of DNA is from 0.00012 mg to about 0.003 mg DNA.

4. The method according to claim 1, wherein said effective amount of DNA is 0.0006 mg of DNA.

5. The method according to claim 1, wherein said patient is a human.

* * * * *